United States Patent [19]
Baer

[11] Patent Number: 5,128,257
[45] Date of Patent: Jul. 7, 1992

[54] ELECTROPORATION APPARATUS AND PROCESS

[76] Inventor: Bradford W. Baer, 420 Claremont Way, Menlo Park, Calif. 94025

[21] Appl. No.: 91,517

[22] Filed: Aug. 31, 1987

[51] Int. Cl.⁵ .............................................. C12N 13/00
[52] U.S. Cl. ................................... 435/173; 435/287
[58] Field of Search ............... 435/6, 173, 172.3, 287, 435/289, 172.2, 172.1; 935/52, 85, 89, 93

[56] References Cited

U.S. PATENT DOCUMENTS 4,695,547  9/1987  Hilliard et al. ................... 435/287
4,764,473  8/1988  Matschke et al. ................ 435/173

OTHER PUBLICATIONS

George W. Bates, "Electrical fusion for optimal formation of protoplast heterokaryors in Nicotiana" Planta. 165 (1985) 217-224.

Berg, H. "Electrotransfection and electrofusion of cells and Electrostimulatior of their Metabolism" Studio Biophsica. vol. 119 (1987) pp. 17-29.

Zimmermann, U. and Vienken J. "Electric Field-Induced Cell to Cell Fusion" J. Membrane Bio. 67, 165-182 (1982).

Primary Examiner—John Niebling
Assistant Examiner—John S. Starsiak, Jr.
Attorney, Agent, or Firm—Flehr, Hohbach, Test, Albritton & Herbert

[57] ABSTRACT

Process and apparatus for electroporation of cell suspensions and cells adhered to a surface wherein at least two simultaneous and directionally distinct electric impulses are used to transfect a biological substance into a cell.

23 Claims, 11 Drawing Sheets

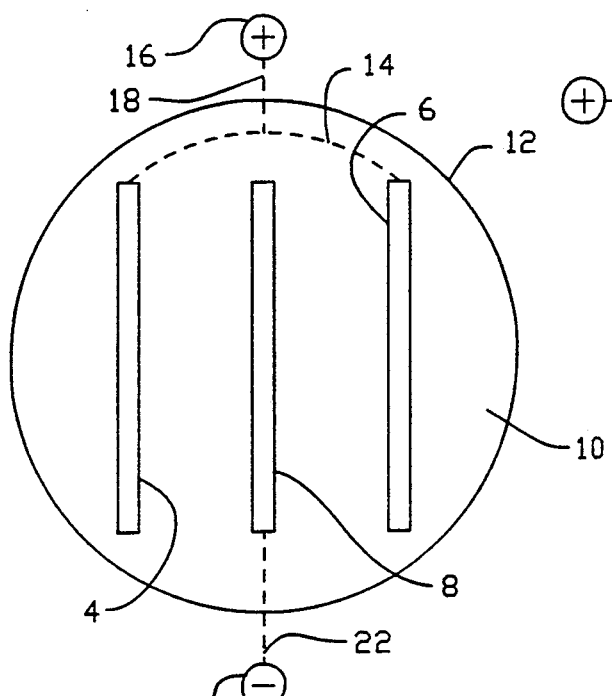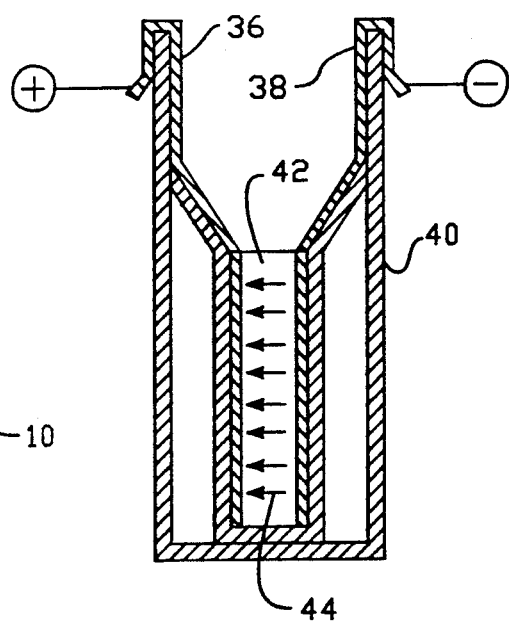
FIG.-1
FIG.-3
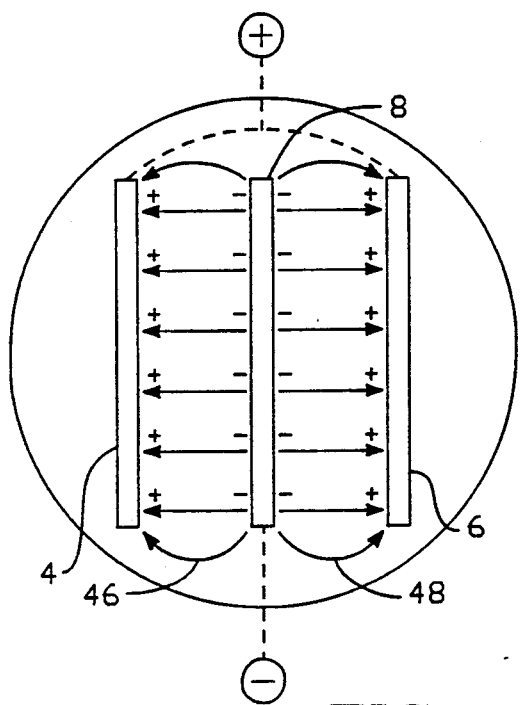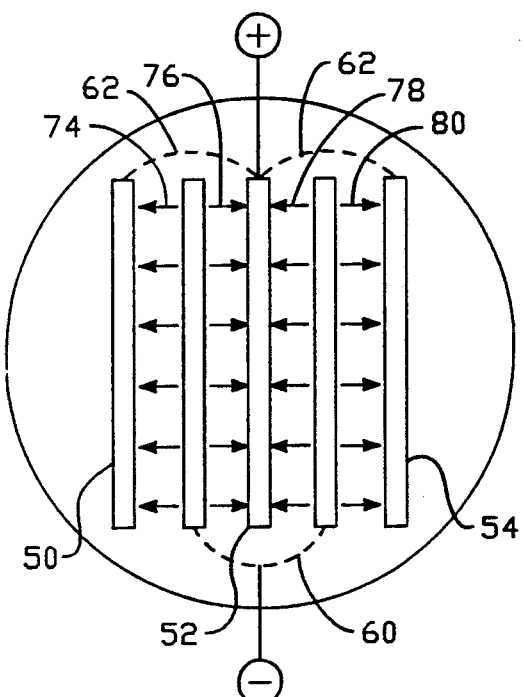
FIG.-4
FIG.-6

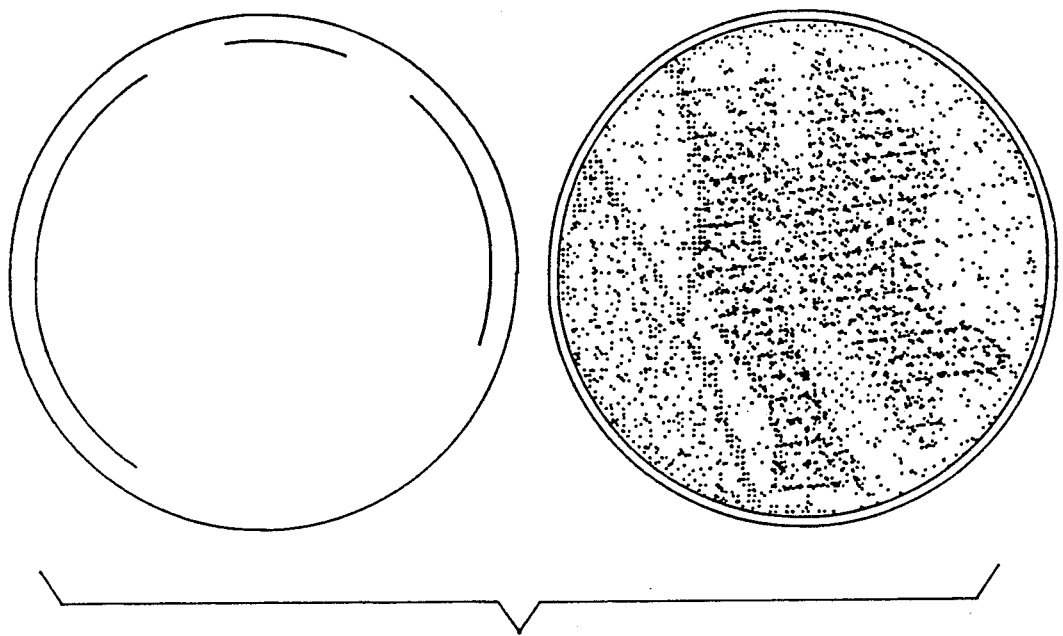
FIG.−15
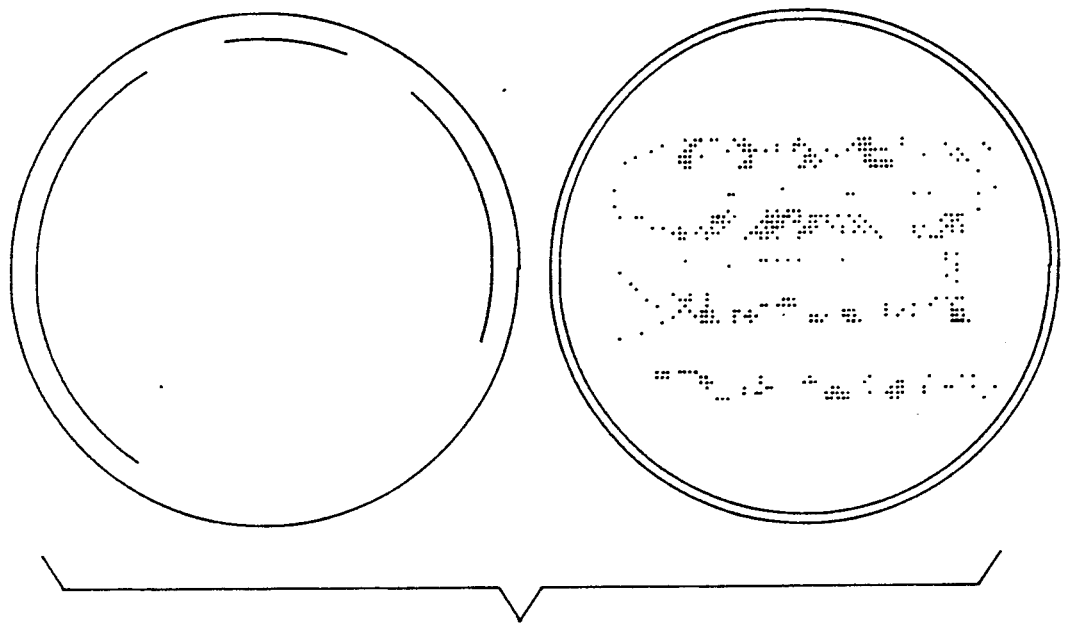
FIG.−16

ELECTROPORATION APPARATUS AND PROCESS

FIELD OF THE INVENTION

The invention relates to electroporation processes to transfect biological substances, including DNA, into cells adhered to a surface or in suspension and to apparatus for performing such electroporation.

BACKGROUND OF THE INVENTION

Electroporation is a technique wherein cells are stimulated to take up material from their surrounding medium by placing the medium containing the material and a suspension of cells between two electrodes and exposing the cells to an electrical impulse (Wong, T. K., et al. (1982) *Biochem and Biophys. Research Commun.* 107, 584–587); Neumann, E., et al. (1982) *Eur. Mol. Biol. Org.* 1, 841–845; Potter, H., et al. (1984), *Proc. Natl. Acad. Sci* 81, 7161–7165). This electrical impulse is most often generated by applying a pulsed direct voltage to the electrodes to produce a pulsed direct current between the two electrodes. A suggested mechanism for this electroporation phenomenon involves the formation of transient holes or pores in the cell membrane through which the surrounding medium containing the material may enter the cell. This is followed by reclosure of the pores and continuation of normal cell growth for those cells which survive the electroporation. This electroporation technique has been most widely applied to the introduction of foreign DNA into cells.

Electroporation of DNA is one of several methods used to introduce DNA into cells (commonly referred to as transfection). Examples of other transfection methods include calcium phosphate co-precipitation (Graham, F. L., et al. (1973), *Virology* 52, 456–467), diethylaminoethyl-Dextran treatment (McCutchan, J. H., et al. (1968), *J. Natl. Canc. Ins.* 41. 351–357), protoplas-fusion (Schaffner, W. (1980), *Proc. Natl. Acad. Sci.* 77, 2163–2167), microinjection (Capecchi, M. R. (1980), *Cell* 22, 479–488) and retrovirus infection (Weiss, R. N., et al. (1982) eds. "RNA Tumor Viruses", Cold Spring Harbor Laboratory, New York).

A common and significant problem with each of these transfection techniques is the low nonreproducible transfection frequency associated with these methods. Moreover, transfection by the calcium phosphate co-precipitation method or by the electroporation of a cell suspension is often not possible since some cell types are killed, or have very low viability when so treated. In addition, some cell types cannot be transfected by the calcium phosphate co-precipitation method or by suspension electroporation, or can only be transfected at extremely low frequencies by these methods.

A significant additional problem is encountered when the suspension electroporation technique is used to transfect cell types which may be grown only when attached to the surface of a culture vessel or to other cells. Prior to electroporation, such cells are treated, either with a proteolytic enzyme such as trypsin or with a chelating agent such as ethylenediaminetetraacetic acid (EDTA), to remove the cells from the culture vessel surface, and from each other, to form a suspension of such cells. The cell suspension together with the DNA to be transfected is transferred to an electroporation device containing two electrodes. A direct electric current is then generated between the electrodes. The cell suspension is then returned to a culture vessel containing selection medium capable of differentiating transfected cells from unsuccessful transformants and dead cells. Such methodology and apparatus are reported by Wong and Neumann (Wong, T. K., et al. (1982) *Biochem and Biophys. Research Commun.* 107, 584–587); Neumann, E., et al. (1982) *Eur. Mol. Biol. Org.* 1, 841–845). As a consequence of such enzymatic or chelation treatment and manipulation, cell viability and transfection frequency are markedly decreased.

The design of these electroporation devices severely restricts their utility. It is not clear whether pore formation results from an interaction between the electric field and induced dipoles in the plasma membrane (Neumann, E., et al. (1982) *Eur. Mol. Biol. Org.* 1, 841–845), a current generated through the cells, transient heat generated by the electrical power through the cells, or a combination of the above effects. Regardless of the mechanism involved, electroporation typically requires the application of about 0.5–10 kilovolts per centimeter between two electrodes to induce transfection at reasonably high frequencies. Thus, the two electrodes have been placed in close proximity to each other, e.g., 2–5 millimeters for use with applied voltages ranging from about 500–5000 volts. Any increase in electrode separation requires a conconmittant increase in applied voltage and has therefore been limited by the availability of power sources capable of delivering such pulsed voltages and the adverse effects of such high voltages on cell viability and transfection frequency. Since transfection presumably occurs between the two electrodes, the electroporation devices heretofore used for transfection have been limited to a relatively small volume wherein the electroporation occurs. Moreover, such electroporation devices have not been adaptable to the electroporation of attachment-dependent cells in situ.

Accordingly, it is an object herein to provide convenient and reproducible electroporation processes for the transfection of cell suspensions and cells adhered to a surface resulting in increased transfection frequencies, including effective transformation of heretofore non-transfectable cell types, and increased viability of transfected cells.

A further object of the invention is to provide electroporation apparatus for transfecting cell suspensions and attachment-dependent cell types in situ without the need for removing such cells from their growth surface.

SUMMARY OF THE INVENTION

The electroporation process of the invention includes adhering cells to the inner surface of an electroporation chamber and contacting such cells with a fluid containing the biological substance to be transfected into the cells. An electric impulse is then passed through the chamber to transfect the substance into one or more of the adhered cells.

The invention also includes an improved electroporation process for transfecting a cell suspension. It comprises contacting an electroporation chamber with a fluid containing a cell suspension and a biological substance to be transfected into the cells and passing at least two simultaneous and directionally distinct electric impulses through the fluid to transfect the biological substance into one or more of the suspended cells.

The invention also comprises an electroporation apparatus which includes fluid containing means, first electrode means disposed in said container means, comprising at least two electrically-connected, spaced electrodes and second electrode means disposed in said container means, comprising at least one electrode. Means are also provided for disposing the first and second electrode means in the fluid containing means. The first and second electrode means are disposed relative to each other such that when an electrically conductive fluid is placed in the container means, at least two simultaneous and directionally distinct electric impulses are generated between the electrodes of the first electrode means and the at least one electrode of the second electrode means when opposite charges are simultaneously applied to the first and second electrode means.

BRIEF DESCRIPTION OF THE DRAWINGS

FIG. 1 depicts a plan view of a three electrode embodiment of the invention.

FIG. 3 depicts an electroporation device employing two electrodes in a plastic curvette and the electric impulse produced therein.

FIG. 4 depicts the electric impulses produced in the three electrode embodiment of the invention.

FIG. 6 is a plan view of the electrode configuration of the apparatus of FIG. 5 and the electric impulses produced.

FIG. 15 demonstrates the transfection of a lawn of CHO cells with SV40-neo.

FIG. 16 demonstrates the transfection of keratinocytes with SV40-neo.

DETAILED DESCRIPTION OF THE INVENTION

Figure 2:
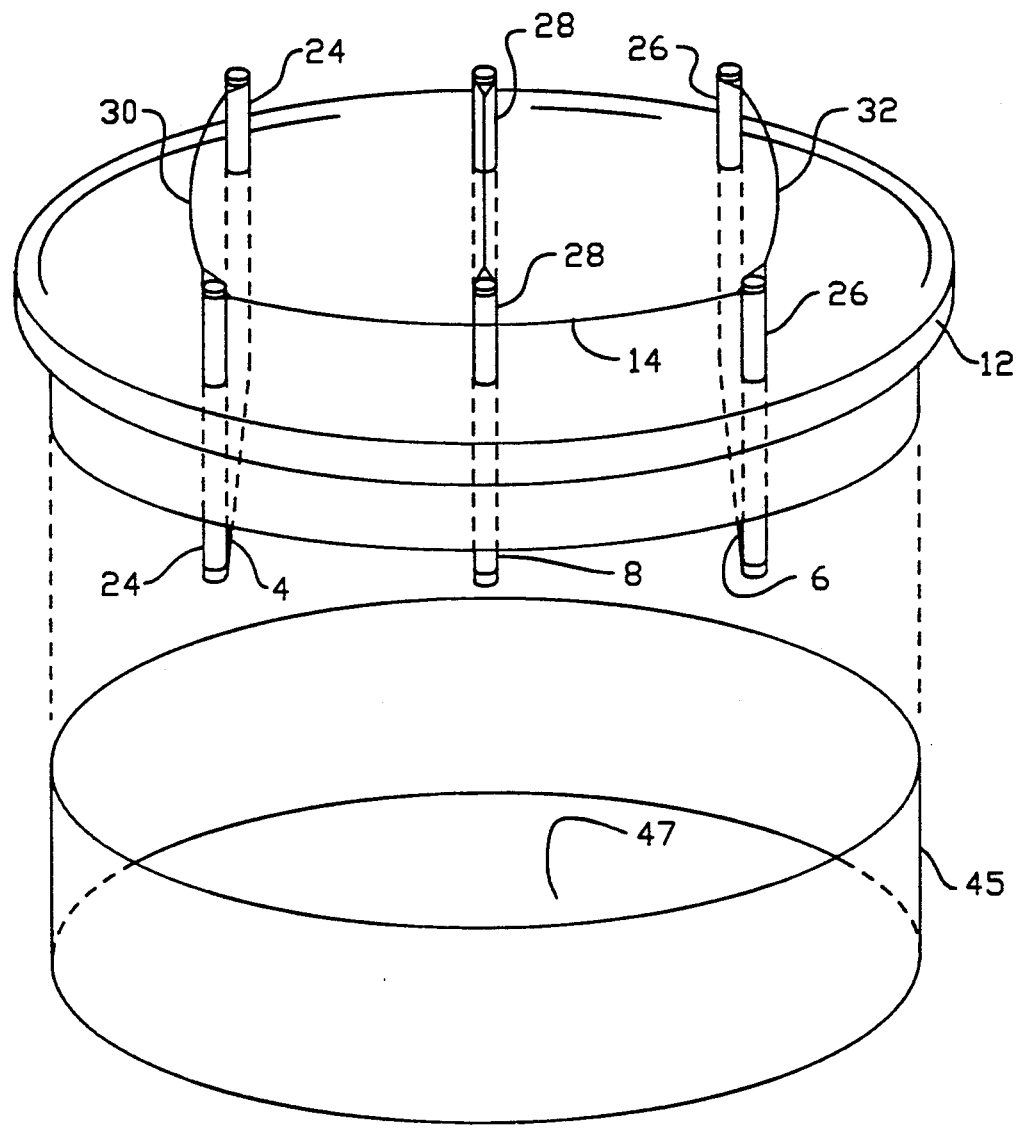
FIG. 2 depicts a perspective view of the three electrode embodiment of the invention.

The inventor has discovered processes whereby attachment-dependent cells can be transfected in situ by exposing such surface-attached cells to one or more simultaneous and directionally distinct electric impulses in the presence of a biological substance, such as a plasmid. The apparatus developed by the inventor generates two or more such electrical impulses and may be used in processes for electroporation of attachment-dependent cells as well as an improved process for the electroporation of cell suspensions.

As used herein "attachment-dependent cells" refers to cells which require a suitable surface to attach in order to grow (Stoker, et al. (1967), *Nature* 215 171-172). Such cells include attachment-dependent cell types such as Chinese Hampster Ovary cells (CHO cells), mouse L-cells, human Hela cells, human 293 kidney cells, normal human epidermal keratinocytes, Buffalo testis cells (BRL3A), rat hepatoma cells and the like. Such attachment-dependent cells are adhered to a surface when they cannot be dislodged from the surface by gentle shaking or washing with liquid (Thilly, W. G. (1986) ed. "Mammalian Cell Technology", Butterworths, Boston). Typically, such cells may be easily removed from the growth surface by treatment with trypsin or EDTA.

Such attachment-dependent cells are typically grown on the inner surface of a container portion of the apparatus of the present invention. Such a container may have the configuration of a petri dish or a tissue culture bottle, which are well known and commonly used for tissue culturing. Containers used in the present apparatus, however, need not be limited to such containers, but may comprise any container configuration suitable for practicing the invention. Typically, the walls of such containers are made of a uniform material to which attachment-dependent cells may adhere. Thus, containers molded from clear plastics such as polystyrene, glass treated with alkali (Rappaport, C., et al. (1960) *Exp Cell Res* 20, 465-510), and FEP-Teflon coated container (Jenson, M. D. (1981) Biotechnol Bioeng 23. 2703-2716) may be used. Since only the inner surface of the container is used for adhering attachment-dependent cells, and in certain embodiments non-attachment-dependent cells, the walls of such containers need not be of uniform construction and may comprise only an inner surface containing such materials. Of course, since the chamber defined by the inner surface of such containers is exposed to electrical impulses, the container or inner surface thereof should be made of substantially non-conductive material such as those previously described.

In some cases the adhering of cells (both attachment-dependent and non-attachment-dependent) to the surface of a container may be induced by treating the surface to increase cell adhesion. Thus, plastics may be treated with sulfuric acid (Maroudas, N. G. (1975), *J. Theor. Biol.* 49, 417-424; Maroudas, N. G. (1977), *J. Cell Physiol* 90, 511-519) or chemically derivitized with glycine (Kuo, M. J., et al. (1981) In Vitro 17, 901-906) to increase cell adhesion. Further, the adhering of cells to the surface of a container, e.g., non-attachment-dependent cells such as the prokaryotes, fungi, yeast, insect cells, plant cells, and mammalian cells such as Raji, Jurkit and U937 may also be induced to adhere to a surface by adhering a protein to said surface having a specific affinity for a cell surface component of a particular cell type (Thilly, W. G. (1986) ed. "Mammalian Cell Technology", Butterworths, Boston). An antibody specific for such cell surface components or specific for a membrane protein may be attached to the inner surface of a container for cell attachment. The methods employed for such antibody or other protein attachment of course will depend upon the material comprising the inner surface of the container and may consist of covalent or electrostatic attachment of an antibody according to protocols well known to those skilled in the art.

The electrodes used in the apparatus of the present invention are made from conductive material such as platinum, gold, aluminum, stainless steel, titanium and alloys thereof, although other conductive materials may be used which, in general, are not toxic to the cells to be electroporated. The above identified specific conductive materials are preferred since such materials are not only non-toxic to most cells but in some cases certain cell-types can actually attach to and grow on the surface of such conductive materials (Dolowy, K. (1980) in Cell Adhesion and Motility, Curtis, A. S. G. and Pitts, J. D., eds., pp. 39–63, Cambridge University Press, Cambridge and New York; Burbidge, C. and I. K. Dace (1984) *Developments in Biological Standardization* 55, 255–259). In general, the electrodes used in the electroporation apparatus are of the same composition to avoid the generation of electric fields and/or currents which may occur when dissimilar electrode material is utilized. The choice of uniform electrode material is especially important in those embodiments wherein cells are grown or maintained on, or in close proximity of, the electrodes.

The apparatus of the present invention overcomes the limitations of previous electroporation devices by providing an electroporation apparatus containing two arrays of electrodes disposed in a electroporation chamber. This arrangement allows for an increase in the effective surface area and volume of the electroporation apparatus. In addition, the configuration of the electrode arrays in the electroporation apparatus may be readily adapted for the electroporation of attachment-dependent cells. The electrodes of a first array are electrically connected to one another such that a voltage applied to one array is uniformly distributed across each of the electrodes in that array. One electrode may be used for the application of an opposite voltage in a second electrode array and in those embodiments wherein there is a multiplicity of electrodes in the second array, such electrodes are also electrically connected.

An embodiment of the electrode component 2 of the electroporation apparatus is shown in FIG. 1. Electrodes 4, 6 and 8 are attached to surface 10 of plexiglass support member 12 by way of conductive posts 24, 26 and 28, respectively, which extend through support member 12 as shown in FIG. 2. Electrodes 4 and 6 are electrically connected through conductor 14 which is attached to one conductive post 24 and 26 of each electrode. To further maximize the uniformity of the electrical impulses in the apparatus conductors 30 and 32 are provided between conductive posts 24 and 26, respectively. Conductor 14 in turn is adapted to be connected to a source of electric charge 16 by way of conductor means 18. Similarly, conductor 34 is provided between conductive post 28 of electrode 8 which is also adapted to be connected to a source of opposite electric charge 20 by way of conductor means 22.

A first electrode means comprises electrodes 4 and 6 electrically connected by conductor 14. A second electrode means, in this embodiment, consists of the single electrode 8. In other embodiments, the second electrode means comprises more than one electrode with each electrode being electrically connected to each other in a manner similar to that shown for the first electrode means. Such embodiments will be discussed in more detail hereinafter.

An example of a previously used electroporation device is shown in FIG. 3. This device contains two electrodes 36 and 38 which are placed against the opposite walls of a flat-sided, open-topped cuvette 40. A cell suspension 42 containing DNA to be transfected is placed in cuvette 40. Upon the simultaneous application of a positive charge to electrode 36 and a negative charge to electrode 38, an electrical impulse designated by the vectors 44 is generated. When electrode component 2 is inserted into petri dish 45, a completed electroporation apparatus is formed as shown in FIG. 2. Prior to insertion, attachment-dependent cells are grown on the bottom inner surface 47 of petri dish 45 to form a lawn of such cells. A similar lawn of non-attachment-dependent cells may also be formed by pretreating the surface as previously described. Alternatively, a suspension of cells may be placed in the petri dish. In each case, DNA or some other biological substance to be transfected into the cells is added to the medium contained in petri dish 45. Electrode component 2 is inserted into the petri dish and a pulsed direct voltage applied to the first and second electrode means. This direct voltage may comprise the application of opposite charge to the first and second electrode means. However, in practice it is to be understood that one of the electrode means often is ground with the other electrode means supplying a positive or negative voltage.

The electric impulses produced in one embodiment of an electroporation device when opposite charge is simultaneously applied to the first and second electrode means is shown in FIG. 4. As can be seen, negative charge accumulates on second electrode means 8 while, simultaneously, positive charge accumulates on first electrode means comprising electrodes 4 and 6. The resultant electric impulse vectors 46 and 48 depict two simultaneous and directionally distinct impulses which can be considered either a direct voltage between electrode 8 and electrode 4 and between electrode 8 and electrode 6 or a direct current between these electrodes if a conductive fluid is placed in the petri dish. This electric impulse, be it a voltage, a current or a combination of both, need not be entirely uniform and in most instances is somewhat deformed as indicated by the curved electric impulse vectors near the ends of the electrodes in FIG. 4.

Figure 5:
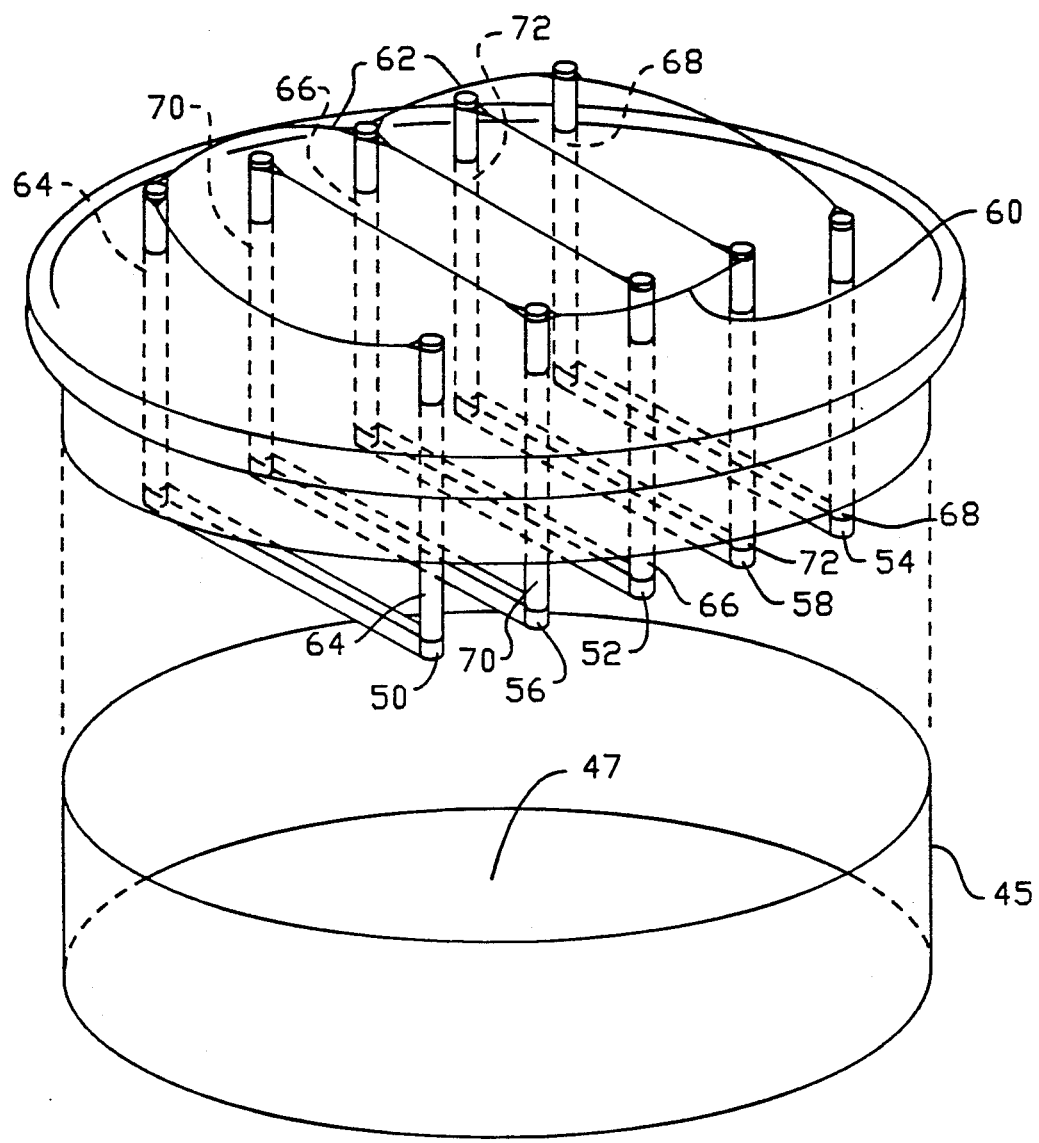
FIG. 5 depicts another embodiment utilizing five parallel electrode bars having alternating polarity.

The preferred embodiment of the present invention is shown in FIG. 5. This embodiment incorporates a design similar to that shown in FIG. 2 except that a five-electrode apparatus rather than a three-electrode apparatus is disclosed. As indicated, electrodes 50, 52 and 54 form a first electrode means which are electrically connected through conductors 62 and through conductive posts 64, 66 and 68. Electrodes 56 and 58 comprise second electrode means which are electrically connected through conductor 60 and conductor posts 70 and 72.

Four discrete simultaneous electric impulses are generated when opposite electric charge is applied to the first and second electrode means as shown by the electric impulse vectors 74, 76, 78 and 80 in FIG. 6.

It will of course be appreciated that the number of electrodes of both electrode means can be increased, thereby decreasing the separation between electrodes and the overall applied voltage applied to produce the necessary voltage/cm required to achieve transfection. At present, the preferred separation of the electrodes between the first and second electrode means is from about 2 mm to 30 mm, most preferably 0.5 to 1.5. It is believed, however, that smaller electrode separations and the use of smaller electrodes themselves may permit even closer spacing of the electrode means. Thus, theoretically, the closest spacing between electrodes of the first and second electrode means may permit even closer spacing of the electrode means may be as close as one or more diameters of the cells to be transfected, e.g., on the order of 10-50 microns.

Figure 7:
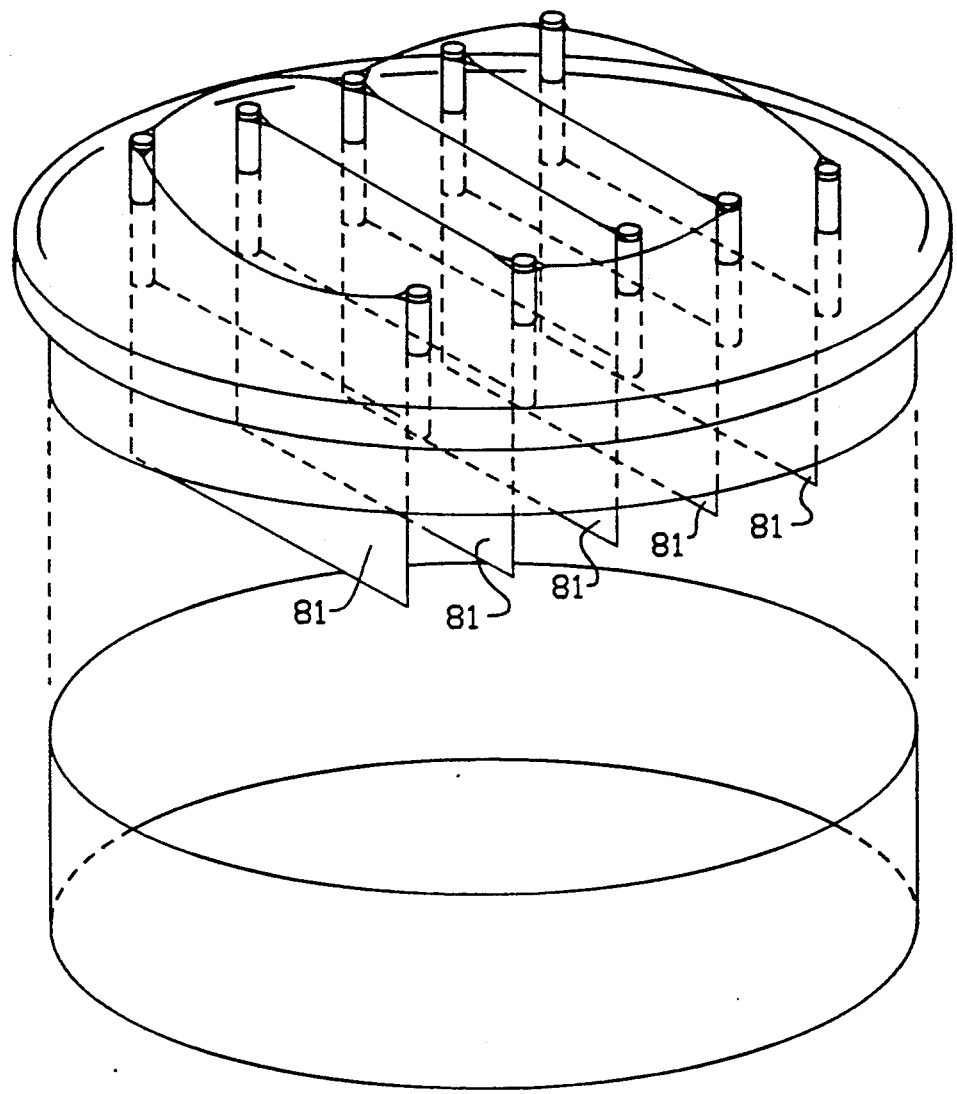
FIG. 7 depicts a five-electrode apparatus utilizing strip electrodes.

Electrodes disclosed in the above embodiments are bar electrodes and are made of square aluminum bar having a width of about 1-2 mm and a length of from between 5-8 centimeters. The particular shape of these electrodes is not deemed to be critical and such electrodes may comprise simple wire electrodes having diameters ranging from 0.1 to 2 mm, most preferably 0.5 to 1 mm, or may comprise strips of electrode material which fill the space defined by the bar electrodes and the conductor posts supporting them. Such strip electrodes preferably have the same length dimensions in these embodiments as the above described bar electrodes and may have a height of about 0.5 cm to 2-3 cm, preferably 1.0 to 2.0 cm, and a thickness of about 0.1 mm to 2.0 mm, preferably 0.1 mm to 0.5 mm. Of course, regardless of the type of electrode used in these particular embodiments, it is preferred that such linear electrodes be interdisposed between each other in a substantially parallel fashion such that alternating charges can be applied to adjacent electrodes. A five electrode embodiment of the apparatus of the invention utilizing strip electrodes 81 is shown in FIG. 7.

Other embodiments of the apparatus of the invention are shown in FIGS. 8 through 14.

Figure 8:
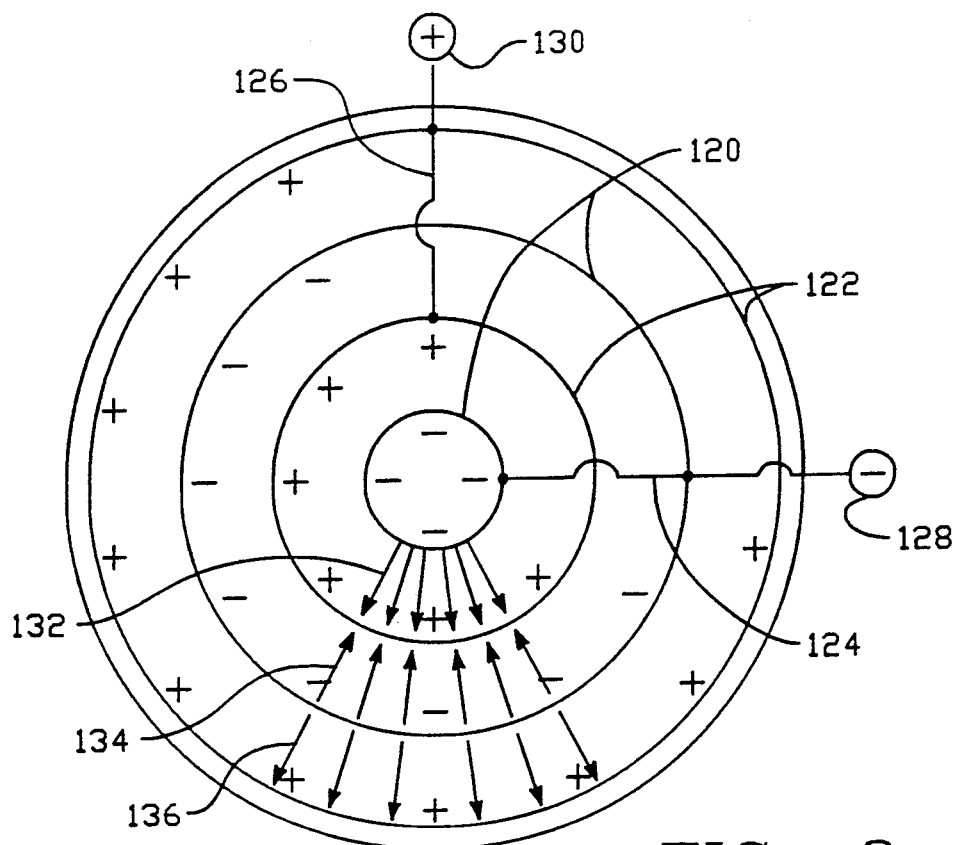
FIGS. 8 and 9 depict two curvilinear embodiments of the invention.
Figure 9:
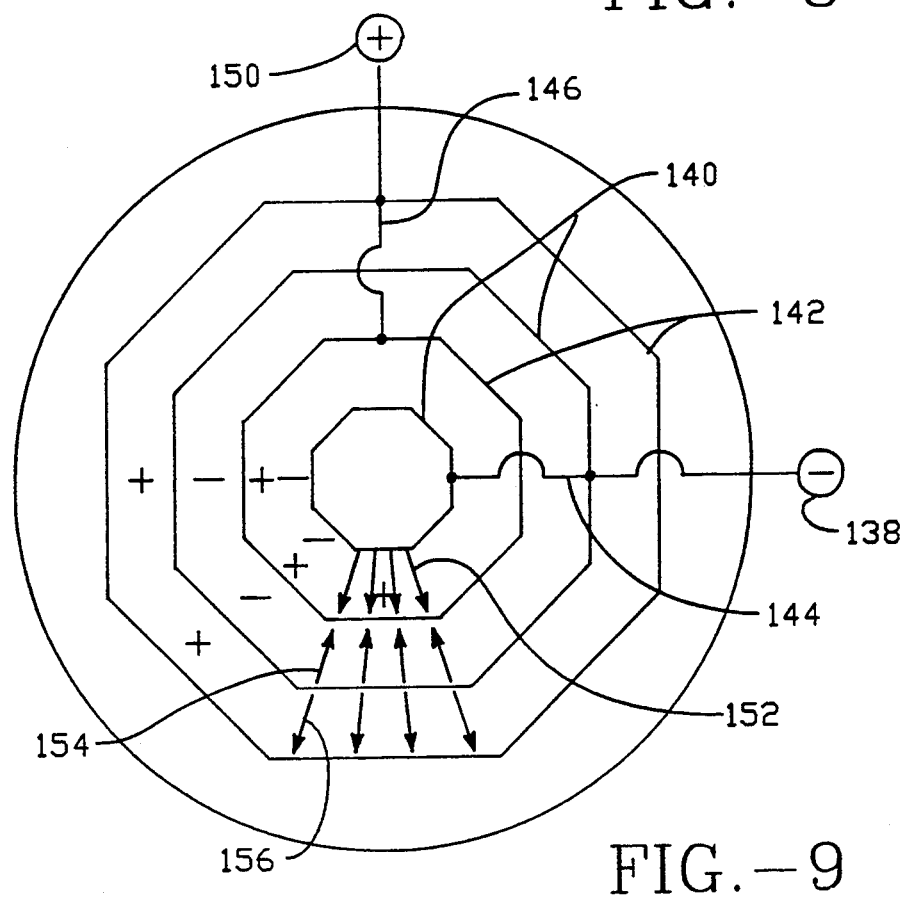

Concentric curvilinear embodiments of the apparatus of the invention are shown in FIGS. 8 and 9. In FIG. 8, concentric curvilinear electrodes 120 comprise a first electrode means whereas concentric curvilinear electrodes 122 comprise a second electrode means. Electrodes 120 are electrically connected by way of conductor means 124 and electrodes 122 are electrically connected by way of electrical conductor 126. Electrical connector 124 in turn is connected to a source of negative charge 128 whereas electrical conductor 126 is connected to a source of positive charge 140. When an electric charge is applied from sources 128 and 140, three simultaneous directionally distinct electric impulses 142, 144 and 146 are generated between the electrodes of the first electrode means and second electrode means.

Similarly, the concentric octagonal curvilinear electrodes 140 and 142 in FIG. 9 comprise first and second electrode means respectively. Electrodes 140 are electrically connected by conductor 144 whereas electrodes 142 are electrically connected by way of conductor 146. Electrical conductor 144 in turn is connected to a source of electric charge 138 whereas electrical conductor 146 is connected to a source of positive charge 150. When an electric charge is supplied by sources 138 and 150, three simultaneous and directionally distinct electric impulses 152, 154 and 156 are produced. The electrode materials in FIGS. 8 and 9 may be made from bars, wires or strips and in the embodiment shown in FIG. 9, may incorporate more than the eight sides of the octagonal curvilinear configuration shown therein.

Figure 10A:
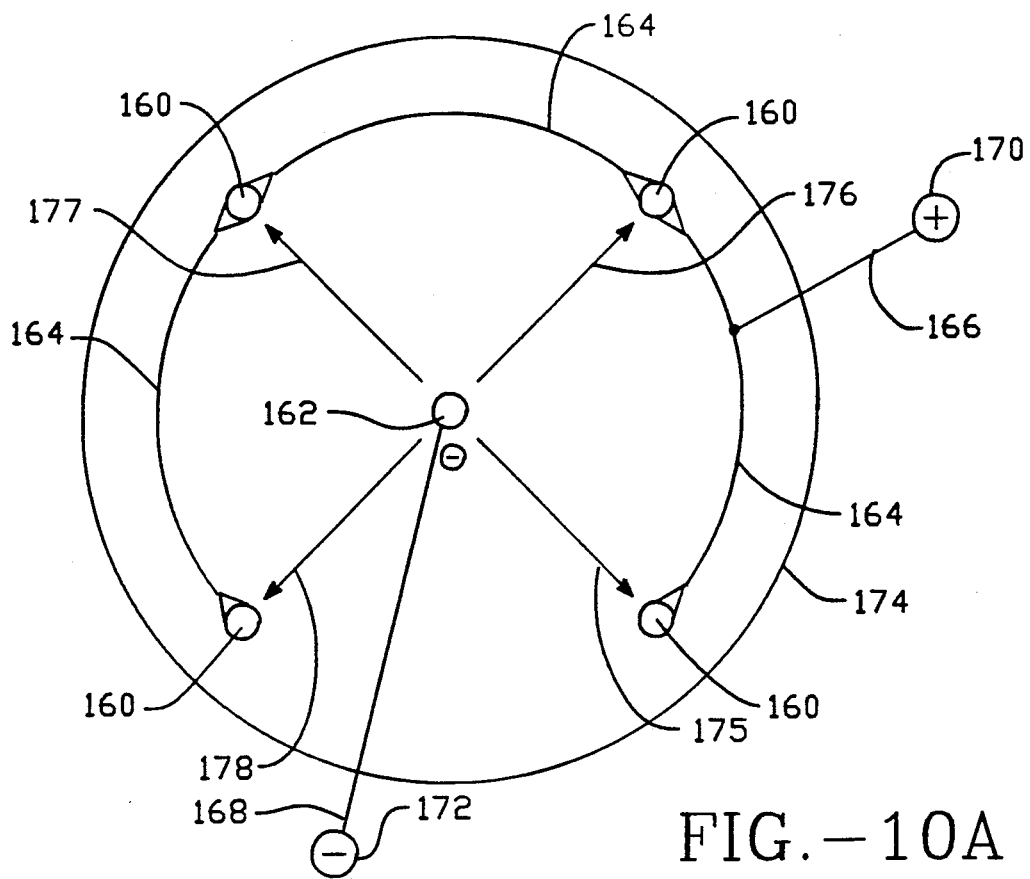
FIGS. 10A, 10B, 11A and 11B depict plan and perspective pin electrode embodiments of the invention.
Figure 10B:
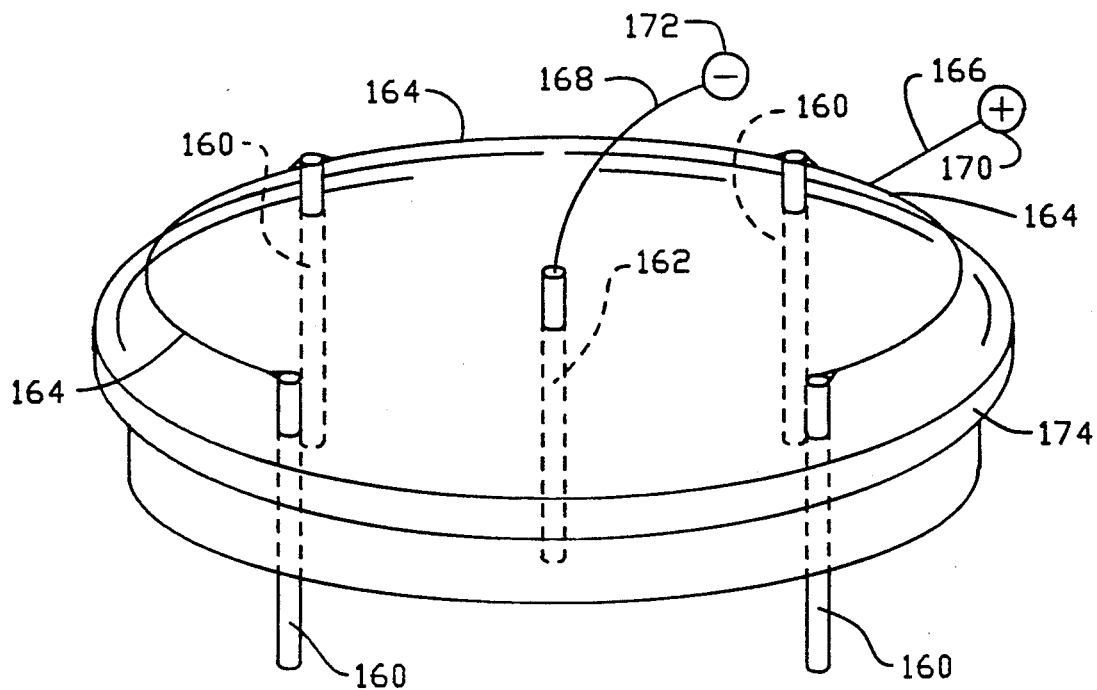

FIGS. 10A and 10B depict an electroporation device which may be inserted into a petri dish and which employs 10 electrodes. A shown in these Figures, four pin electrodes 160 are inserted through and attached to support member 174 such that they are spaced substantially equidistant from each other around the central electrode pin 162 which is also inserted through and attached to support member 174. The pin electrodes 160 are electrically connected through conductors 164 which in turn is connected to the source of positive charge 170 by way electrical conductor 166. Electrode pin 162 is electrically connected to a source of negative charge 172 by way of electrical connector 168. Electrodes 160 comprise a first electrode means whereas electrode 162 comprises a second electrode means. When opposite electric charges are applied to such first and second electrode means, four simultaneous and directionally distinct electric impulses 175, 176, 177 and 178 are produced.

Figure 11A:
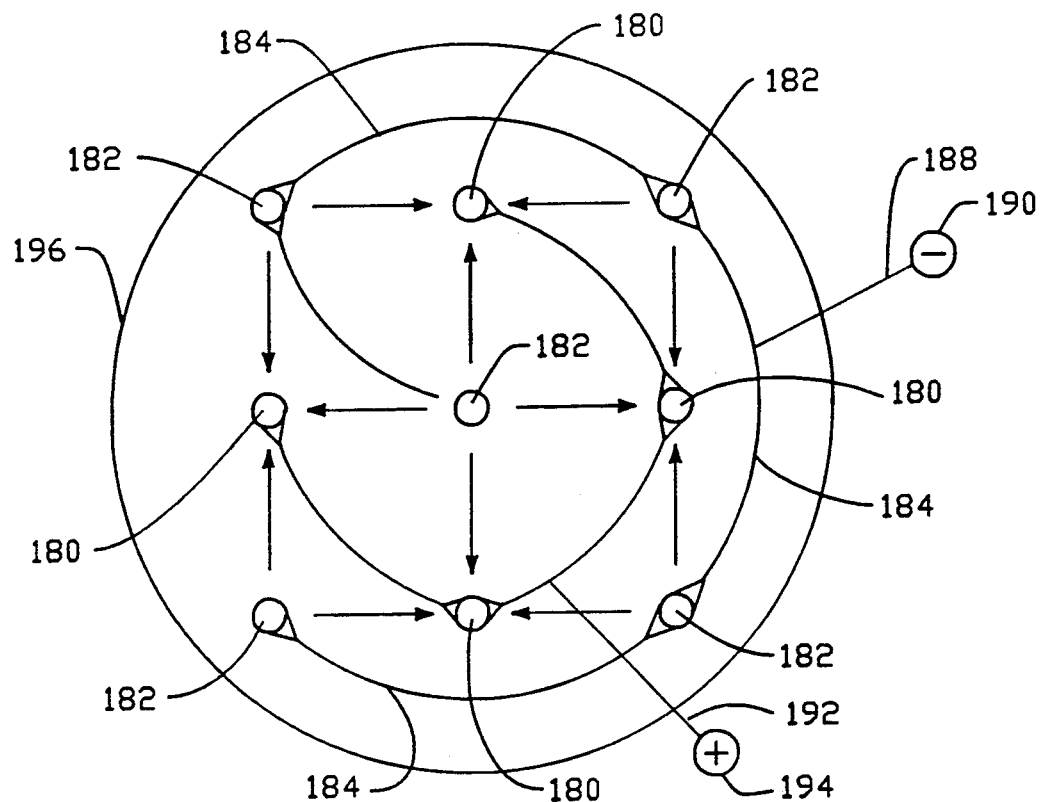
Figure 11B:
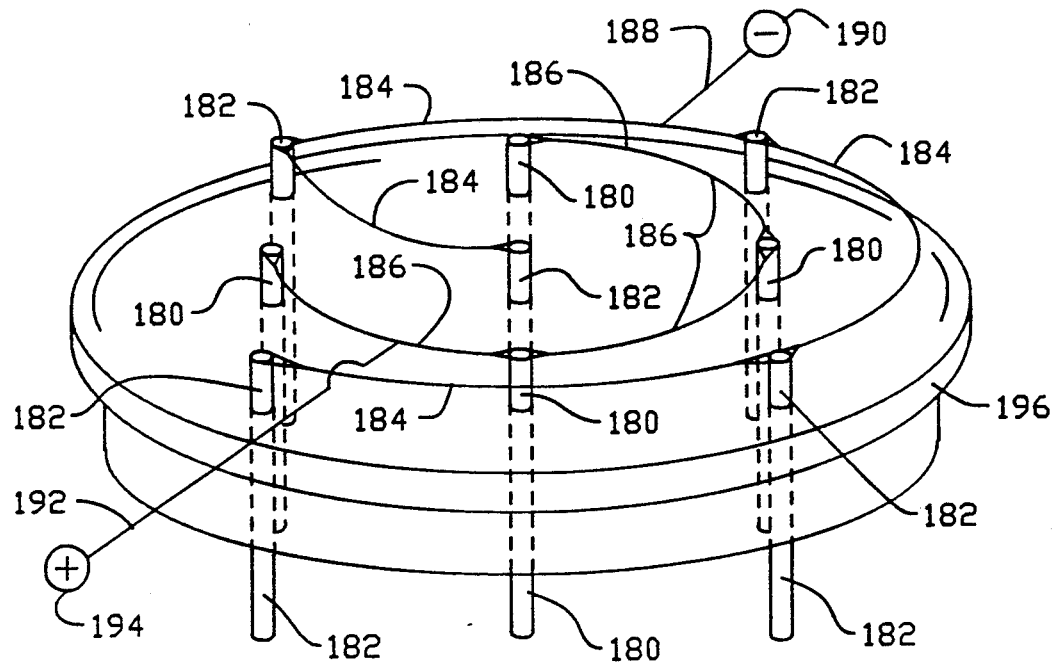

FIGS. 11A and 11B disclose a further embodiment of the apparatus of the invention which utilizes a more complex configuration of pin electrodes. Four pin electrodes 180 are disposed through and attached to support member 184 as shown in FIGS. 11A and 11B. The five pin electrodes 182 are disposed through and attached to support member 196 also substantially as shown in FIGS. 11A and 11B. Pin electrodes 180 are electrically connected by way of conductors 186 to produce a first electrode means and pin electrodes 182 are electrically connected by way of electrical conductors 184 to form a second electrode means. The first electrode means is connected to a source of positive charge 184 by way of conductor 192 whereas the second electrode means is connected to a source of negative charge 190 by way of electrical conductor 188. When an opposite electric charge is applied to the first and second electrode means, the simultaneous and directionally distinct electrical impulses as represented by the vectors shown in FIG. 11A are produced.

Figure 12:
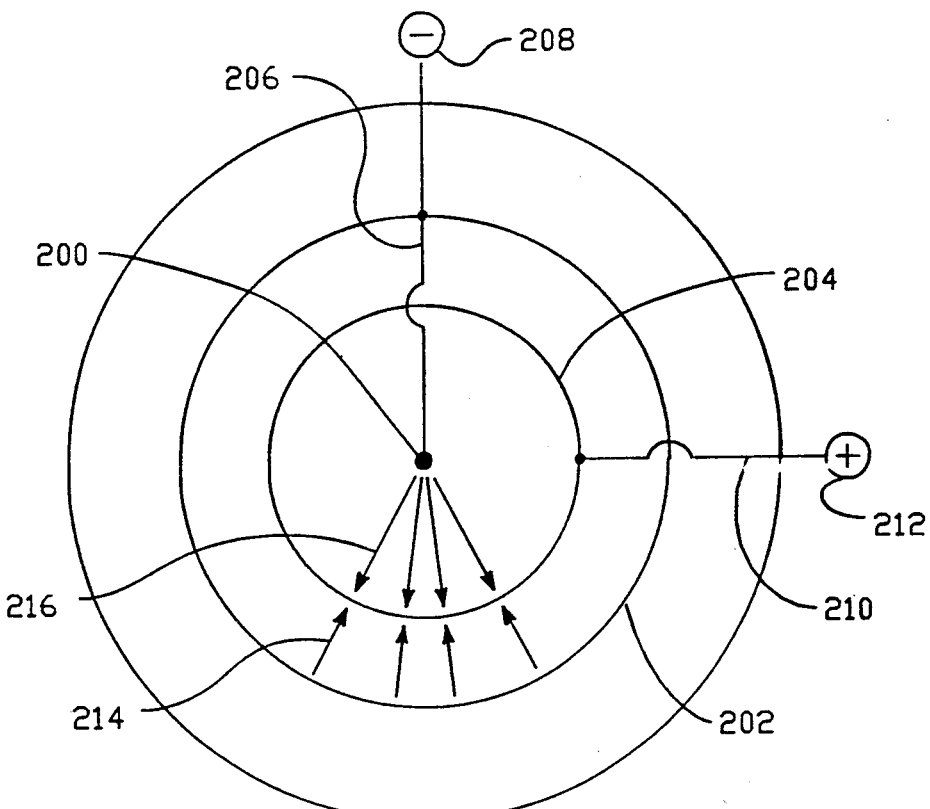
FIG. 12 depicts a hybrid embodiment incorporating pin and curvilinear electrodes.

FIG. 12 depicts a hybrid electrode configuration employing curvilinear electrodes and pin electrodes. A first electrode means is formed by electrically connecting pin electrode 200 with curvilinear electrode 202 by way of electrical conductor 204. Electrical conductor 204 is connected by way of conductor 206 to a source of negative electric charge 208. A second electrode means comprises curvilinear electrode 210 which is concentrically located between pin electrode 200 and curvilinear electrode 202. This electrode is connected by way of conductor 210 to a source of positive charge 212. When a opposite electric charge is applied to the first and second electrode means the simultaneous and directionally distinct impulse vectors 214 and 216 are produced.

In each of these embodiments, the size and separation of the electrodes are preferably those as described for the embodiments of FIGS. 2 and 5. Further, the spacing between the electrodes of the first and second electrode means are also preferably as described for the embodiments in FIGS. 2 and 5.

Figure 13:
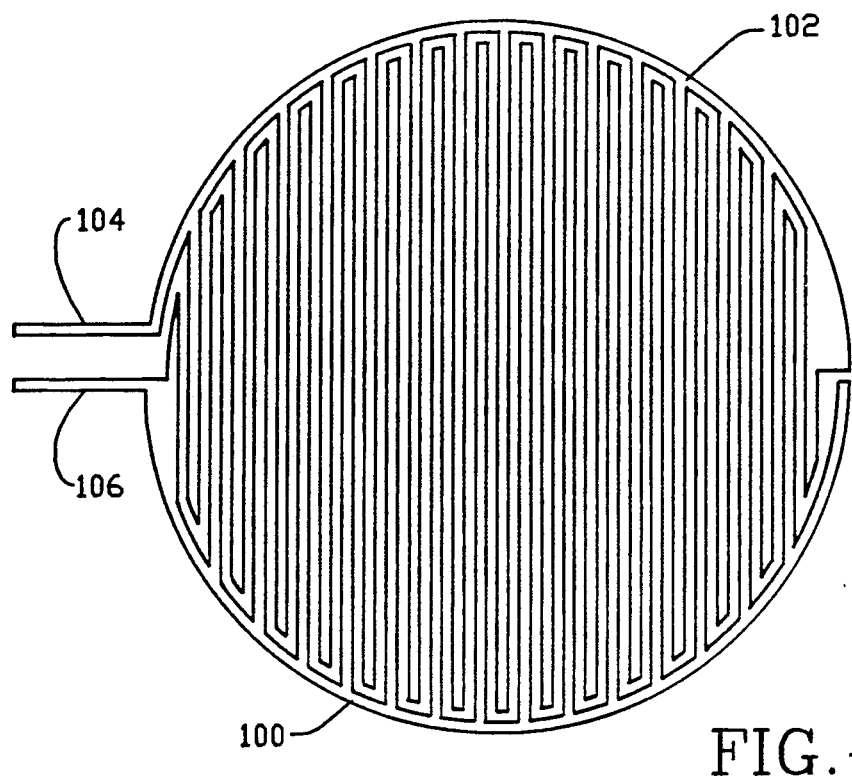
FIG. 13 depicts the electrode pattern for an embodiment formed by the vapor deposition of metal on a surface.
Figure 14:
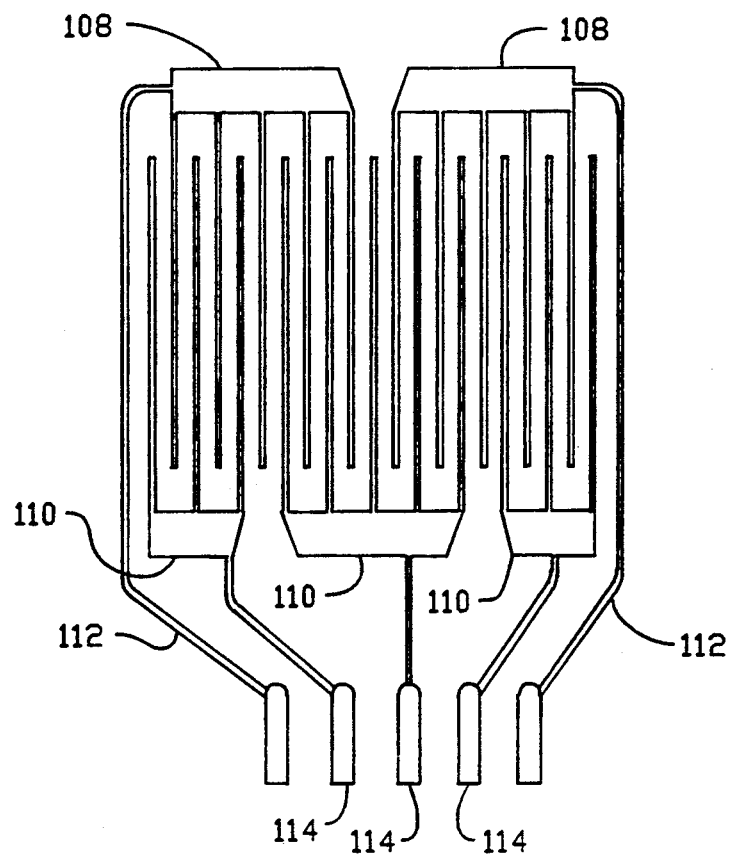
FIG. 14 depicts the electrode pattern for an embodiment formed by etching aluminum from a laminated surface.

Further embodiments of the invention are shown in FIGS. 13 and 14 which depict electrode patterns which may be formed on a support member having a substantially non-conductive surface. When so formed, electroporation inserts are produced which may be inserted and in some cases bonded with heat or ultrasonics in, for example, a petri dish or tissue culture bottle with appropriate electrical connections to apply electrical impulses across the electrodes. Alternatively, the flat support (e.g., mica polyester or polystyrene) can be molded with heat to form the vessel itself.

The electrode configuration shown in FIG. 13 is particularly well suited for insertion into a petri dish or for direct application onto an inner surface of a petri dish. Thus, when formed as an electroporation insert, copper vapor or other metallic vapor such as aluminum, gold, platinum and nickel, may be deposited on a flat planar surface of non-conducting material such as mica polyester or polystyrene. When so deposited, for example, using a mask to generate the electrode array pattern shown in FIG. 13, first electrode means 100 and second electrode means 102 are formed such that multiple directionally distinct electric impulses are produced when opposite charges are applied to electrode leads 104 and 106.

FIG. 14 depicts the electrode pattern of first electrode means 108 and second electrode means 110 formed by selectively etching a metal surface attached to a substantially non-conductive flat planar surface. In this embodiment, metal such as aluminum, may be deposited as a solid continuous sheet on surfaces made from mica polyester. When an opposite charge is applied to electrical connections 112 and 114 multiple directionally distinct electrical impulses are formed between the electrodes of the first electrode means 108 and the second electrode means 110.

In each of the embodiments of FIGS. 13 and 14, the electrode material is preferably about 1 to 100 thousandths of an inch thick with each electrode having a width of about 10 $\mu$m to 2 mm, preferably 0.1 mm to 1 mm and a spacing between the electrodes of about 10 $\mu$m to 2 mm, preferably 0.1 mm to 1 mm. Since these electrodes are substantially closer together than in the previous embodiments, the voltage applied across the first and second electrode means is substantially lower than that in the other embodiments. Thus, voltages of between 1 to 500 volts, preferably 10 to 100 volts, are applied across the electrodes of the first and second electrode means. The total area of the electrode array will be limited by the current capacity of the power supply.

The methods used to produce such vapor deposited electroporation inserts and selectively etched electroporation inserts are well known. Thus, metal deposition may be carried out according to the methods disclosed by P. Gise and R. Blanchard in "Modern Semiconductor Fabrication Technology", Chapter 8 (Prentice-Hall, England Cliffs, N.J., 1986), and A. B. Glaser and G. E. Subak-Sharpe in "Integrated Circuit Engineering", Chapter 5 (Addison-Wesley, Reading, Mass., 1977) and selective etching of laminated material may be carried out according to the methods disclosed by C. F. Coombs, Jr., ed., in "Printed Circuit Handbook", Chapters 1 and 8 (McGraw-Hill, New York, N.Y., 1976). Such methodology, however, is not limited to the production of electroporation inserts, but may be used to produce first and electrode means on, for example, the inner surface of a petri dish, the inner surface of a tissue culture bottle or other appropriate container means for carrying out electroporation.

Electroporation inserts having a density greater than that of the media used for electroporation and which are relatively rigid may be directly inserted into an electroporation chamber with appropriate electrical connections. However, in some instances, the electroporation insert may comprise a thin flexible material which may be attached to the inner surface on electroporation container such as a petri dish or tissue culture bottle by way of non-toxic adhesives. Alternatively, such flexible inserts may be retained on the bottome surface of an electroporation container by way of a second insert designed to hold the electroporation insert in place along the perimeter of such inserts. Thus, a second insert for use with an embodiment as in FIG. 13 could comprise a flexible split O-ring having an outer diameter corresponding to the inner diameter of a petri dish into which the electroporation insert of FIG. 13 may be placed. Yet another alternative is to bond the insert to the vessel using adhesives or treatment with heat and/or ultrasonic waves.

Electroporation of attachment-dependent cells may be carried out in any of the above described electroporation devices, although the five electrode device shown FIGS. 5 and 6 is preferred. As used in the experiments, the electrodes are in direct contact with the bottom surface 47 of petri dish 45. Generally, in situ electroporation is achieved by plating attachment-dependent cells to a density of about $10^4$ per cm$^2$ in the bottom of petri dish 45. After approximately two days growth, the cells are rinsed in phosphate buffered saline (PBS: 0.15 molar NaCl 0.015 molar NaPO4 pH 6.8), or another buffer of choice, and the DNA to be transfected is added to the electroporation culture vessel. The DNA is also dissolved in PBS at a concentration of approximately 0.5 to 15 micrograms per ml. Approximately 1 ml of the DNA solution is used per 50 square centimeters of petri dish surface.

The cells may be electroporated with a variety of power pulses to produce voltage gradients of about 200-10,000 volts/cm, preferably 200-2000 volts/cm. One type of power pulse is that generated by the discharge of a high current capacitor such as that contained in an ISCO400 power supply. The voltages in the range of 200 to 2000 volts are typically discharged from the power supply resulting in a voltage gradient of approximately 200 to 2,000 volts per centimeter. A second type of power pulse is a square wave such as that generated by a Cober5000 power supply which produces voltages of approximately 200 to 2000 volts. The pulse width in each case is from about 0.1 to 100 milliseconds, preferably 1 to 10 milliseconds. The currents generated by such voltage will depend upon the conductivity of the medium between the electrodes.

For a transient expression studies, serum-free medium containing growth factors is added after electroporation (0.1 ml per cm$^2$) with additional medium being added on each of the next six days (0.02 ml per cm$^2$). Aliquots (approximately 0.5 ml) may be removed for protein immunoassay or other analysis on various days during t is time period.

The levels of protein produced by plasmids encoding such proteins are approximately 3-5 fold greater using the in situ electroporation technique then the levels of obtained with either the calcium phosphate or the suspension electroporation method described herein. This improved level of expression is in all likelihood due both to the improved transfer of DNA into the cells and to improved viability of the cell after transfection.

Selection of viable and successful transformants can be achieved by employing a selection marker on the plasmid being transfected into a particular cell line. For example, genes encoding for dihydrofolatereductase (DHFR) or thymidine kinase (TK) may be included in the plasmid. In addition, selection markers such as resistance to neomycin or derivatives thereof (e.g., G418), hygromycin B and other antibiotics may also be readily employed. Generally, after electroporation, approximately 12 ml of normal media containing 10% fetal calf serum is added to the culture. After two days of growth the medium is replaced with selective medium containing 10% dialized fetal calf serum. This selective medium is chosen based on the selection characteristic being utilized and selects those cells that have stably integrated a functional plasmid into the transfected cell. Transfection frequency can be determined from the number of colonies arising from growth in such selection media and can be recorded by staining the cells with crystal violet.

In situ electroporation has been used to transfect cell lines which are difficult or impossible to transfect by other techniques. For example, primary human keratinocytes been transfected with this method with pSV40-neo. See Example 3.

In situ electroporation is especially well suited to maximize cell viability after electroporation since in some situations alternate buffer solutions are used during transfection which may be toxic or partially toxic to the cells compared with normal growth medium. Thus, when such toxic media are used during electroporation, the surface attached cells may be exposed to such solutions for relatively short periods of time since removal of growth medium, rinsing, exposure to toxic medium and the application of electric pulse or pulses and readdition of growth media can be achieved in approximately two minutes or less. Other previous techniques require longer exposure times to such toxic solutions, especially where cells must be trypsonized to be removed from the growth surface.

In addition, the decreased exposure time to transfection solutions other than growth medium can be utilized to advantage with buffers of low ionic strength. Thus, low ionic strength buffer, even those buffers generally regarded as not being compatible with cell viability over long exposure times, can be used during electroporation. These buffers permit the use of a lower voltage and a shorter duration pulse than that required for higher ionic strength solutions. The overall current through the solution is thus decreased thereby reducing the overall heat generated during electroporation with concomitant increases in cell viability. Further, the current is more effectively directed through the cells because of their inherently higher ionic strength.

Embodiments of the apparatus of the invention employing more than two electrodes of opposite polarity may be used in practicing the improved process of the invention wherein cell suspensions are successfully transfected with DNA.

Suspensions of cells, especially non-attachment dependant cells, can be electroporated either after rinsing in PBS or another buffer of choice (by centrifugation at 200 g for two minutes and decantation) or directly in growth medium. The suspension of cells (1 ml solution and $10^6$ cells per 50 $cm^2$ surface area) and containing 0.5 to 15 micrograms of DNA per ml, is electroporated as described herein for attached cells.

The biological substance which may be transfected according to the processes of the invention include plasmid DNA, genomic DNA, immunoglobulins or other macromolecules. Samples of plasmid DNA include SV40-neo, SV40-TGF$\beta$, SV40-CAT, or any plasmid DNA or expression vector generally used by those skilled in the art. Genomic DNA may be derived from any prokaryote or eukaryotic source. In general, the DNA is extracted so as to maximize the length of the DNA transfected into the cell. Maddon, et al. (1985) Cell, 42, 913-104. In some situations, however, the DNA may be digested with one or more restriction endonucleases, especially when it is known that such digestion does not destroy the integrity of a gene of interest.

The following examples are set forth for the purposes of example only and are not to be construed as any limitation on the scope of the invention.

EXAMPLE 1

Chinese Hampster Ovary cells ("CHO" attachment-dependent cell line, Urlaub, et al. (1980), PNAS 77, 4216) were plated on polystyrene petri dishes (100 mm diameter) at a density of $2 \times 10^4$ cells/$cm^2$. After two days of growth in Minimum Eagle's Medium (MEM) containing 10% fetal bovine serum (FBS), the cells were rinsed with 5 ml phosphate buffered saline (PBSi 0.15 m NaCl-15 mm $NaPO_4$, pH 6.8). Two ml PBS containing 10 micrograms of the expression plasmid SV40-TFG$\beta$ (SV40 promoter and the gene coding for transforming growth factor beta; Derynek, et al. (1985), Nature, 316, 701-705; Crowley, et al., 1983) was added to the rinsed cells, the electroporation device shown in FIG. 5 placed over the cells, and four 2000 volt pulses of direct current (at 15 seconds intervals, each lasting one msec.) were applied to the electrodes of the electroporation device with a Cober, Model 605 Pulse Generator (Cober Electronics, Inc., Stamford, Conn.). Ten ml of MEM medium (without serum) was added to the dish, the cells allowed to grow for two days, the media removed, and assayed for the presence of TGF$\beta$ protein using a radioimmune assay (Yalow, R. S., et al. (1960), J. Clin. Invest. 39, 1157; Yalow, R. S. (1978), Science 200, 1236-1245) incorporating an antibody raised against TGF$\beta$ (R&D Systems, Minneapolis, Minn.).

The results are shown in Table I, along with a control carried through the same procedure without the addition of the expression plasmid. Clearly, a significant level of TGF$\beta$ immunoreactive material was produced, showing efficient transient expression of the plasmid transfected using this apparatus.

TABLE I

| TGF$\beta$ Detected from CHO Cells Transfected With and Without SV40-TGF$\beta$ | |
|---|---|
| Transfected Condition | TGF$\beta$ Detected in Medium |
| SV40-TGF$\beta$ expression plasmid | 420 ng/ml |
| No plasmid | not detected |

EXAMPLE 2

Transfection of Surface-Attached CHO Cells with SV40-neo

CHO cells were plated at a density of $10^4$ cells/$cm^2$ and electroporated as in Example 1, except that the expression plasmid SV40-neo (Colbere-Garapin, F., et al. (1981), J. Mol. Biol. 50, 1-14; Southern, P. J., et al. (1982), J. Mol. Appl. Genet. 1, 327-341) was used. After electroporation, 10 ml of MEM containing 10% FBS was added. After two days growth, fresh MEM was added containing 0.4 mg/ml neomycin (selective medium). Every third day the old selective medium was removed and fresh selective medium was added. After 12 days in selective medium, the plate was rinsed with PBS and stained with crystal violet in order to reveal the surviving cells.

The results in FIG. 15 show that the cell plate receiving the SV40-neo expression plasmid (FIG. 15 right) contained a large number of colonies (about 2,000), whereas the control plate (FIG. 15 left) which did not contain the SV40-neo plasmid during electroporation showed contained no colonies. demonstrating efficient stable transfection using the device.

EXAMPLE 3

Transfection of Surface-Attached Keratinocytes with SV40-neo

Normal human epidermal keratinocytes (attachment-dependent, Clonetics Corp., Boulder, Colo.) were plated, electroporated, selected, and stained as in Examples 1 and 2, except that the expression plasmid SV40-neo was used and the selective medium contained 0.6 mg/ml neomycin. FIG. 16 shows the stained petri dishes. The dish on the left did not contain the SV40-neo plasmid during electroporation whereas the dish on the right did. This demonstrates that the cells which survived did no by virtue of stably receiving the SV40-neo plasmid which contains a gene conferring neomycin resistance. These cells are normally very difficult to transfect by other methods, though retroviral transfection has reportedly been successful (Palmer, T. D., et al. (1987) PNAS 84, 1055–1059). The pattern of surviving cells, indicates that cells between the five element electrode are preferentially transfected.

EXAMPLE 4

Transfection of Jurkit Cell Suspension with SV40-CAT

Figure 17:
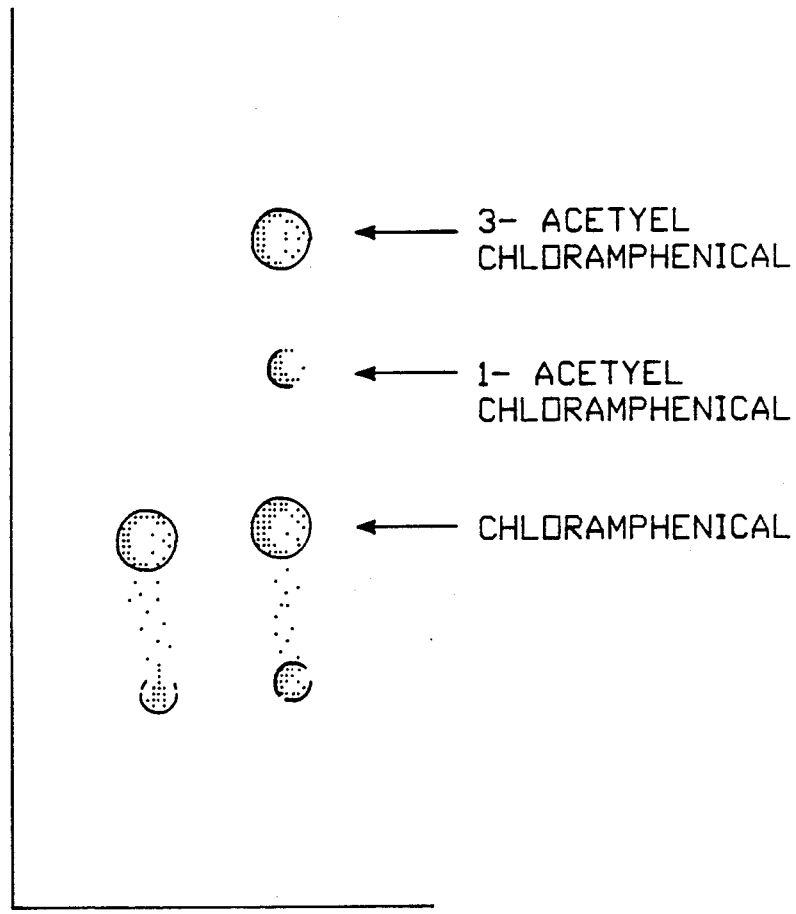
FIG. 17 demonstrates CAT activity of Jurkit cells transfected with SV40-CAT.

Jurkit cells (suspension, Gillis, S., et al. (1980) *J. Exp. Med.* 152, 1709–1719) were washed in PBS, suspended in 2 ml PBS, and the suspension ($2 \times 10$ cells) added to a 100 mm diameter petri dish. Cells were electroporated as in Example 1 except the SV40-CAT plasmid (Gorman, C. M., et al., (1982), *Mol. Cell. Biol.* 2, 1044–1051) was used for transfection. This plasmid encodes for, inter alia, the expression of chloramphenicol acetyl transferase ("CAT") which transfers an acetyl group from acetyl coenzyme A to the antibiotic chloramphenicol. This enzyme maker is useful because it is normally absent from mammalian cells. Ten ml of MEM containing 10% FBS was added and after two days of growth the cell supernatants were assayed for CAT activity (Gorman, C. M., et al., (1982), *Mol. Cell. Biol.* 2, 1044–1051). The thin layer chromatogram (FIG. 17) shows acetylation of chloramphenicol and thus clearly demonstrates transient expression of the SV40-CAT plasmid transfected into these cells with this electroporation device.

EXAMPLE 5

Transfection of Raji Cell Suspension with SV40-TGF$\beta$

Raji cells (suspension 106 cells/ml, ATCC CCL 86) 2 ml in MEM - 10% FBS were added to a 100 mm petri dish. Ten micrograms of the plasmid SV40-TGF$\beta$ was added and the cells electroporated as in Example 1. Ten ml of serum-free MEM was added and the cells allowed to grow for two days. Cell supernatants were assayed by the immunoassay, as in Example 1. The results in Table II show that after electroporation of SV40-TGF$\beta$ into Raji cells in the presence of growth medium$\beta$ using this device clear transient expression of TGF occurs.

TABLE II

| Raji Cells Transfected Directly in Growth Medium With and Without SV40-TGF$\beta$ | |
|---|---|
| Transfection Condition | TGF$\beta$ Detected in Medium |
| SV40-TGF$\beta$ expression plasmid | 18 ng/ml |

TABLE II-continued

| Raji Cells Transfected Directly in Growth Medium With and Without SV40-TGF$\beta$ | |
|---|---|
| Transfection Condition | TGF$\beta$ Detected in Medium |
| No plasmid | not detected |

EXAMPLE 6

Comparison with Other Transfection Methods

CHO cells were transfected with 10 micrograms SV40-TGF$\beta$ as described in Example 1. CHO cells were also transfected with 10 micrograms SV40-TGF$\beta$ by suspension electroporation method of Potter, et al. (1984), *Proc. Natl. Acad. Sci.*, 81, 7161–7165, the calcium phosphate method of Graham, et al. (1973), *Virology*, 52, 1456–1467 and DEAE dextran method of McCutchan, et al. (1968), *J. Natl. Canc.*, 41, 351–357. After transfection, the cultures were maintained in 100 nm diameter petri plates for two days in MEM - 10% FBS. SV40-TGF$\beta$ was used in all cases.

The immunoassay of Example 1 was used to measure the amount of TGF$\beta$ in the media. The results are shown in Table III and demonstrate that the electroporation of surface attached CHO cells using the process and apparatus of the invention gives higher levels of gene product than the other methods. This is likely, due to a combination of increased transfection frequency and increased cell viability. The number of cells and the number of cells having apparent viability at the time of harvest for assay was greatest for attached cells electroporated in situ, indicating a less toxic effect by this transfection method compared to the other methods.

TABLE III

| Comparison of Transfection Methods of CHO Cells with SV40-TGF$\beta$ | |
|---|---|
| Method | Concentration of TGF$\beta$ in Media |
| in situ electroporation of attached CHO cells | 672 $\mu$g/ml |
| Suspension electroporation of CHO cells (2 electrode cuvette) | 253 $\mu$g/ml |
| Calcium phosphate co-precipitation method | 116 $\mu$g/ml |
| DEAE transfection method | 78 $\mu$g/ml |

A direct comparison of suspension electroporation in the two electrode cuvette of Table III versus the five electrode embodiment of the present invention has also been made. Raji cells were suspended in growth medium to a concentration of about $10^6$ cells/ml. A suspension of such cell was placed in the two electrode cuvette and in the five electrode embodiment of the present invention. The plasmid pTK-HYG containing the selection characteristics for hygromycin B and using the thymidine kinase promoter (Santerre, R. F., et al. (1984) *Gene*, 30, 147–156; Sugden, B., et al. (1985) *Mol. and Cell. Bio*, 5, 410–413) was added to a concentration of 5 micrograms per ml. After electroporation, and selection for hygromycin resistance, it was determined that 20–40% of the Raji cells electroporated in the five electrode embodiment of the invention were transformed with plasmid pTK-HYG. The Raji cells electroporated in the two electrode cuvette apparatus, however, were not transfected at any detectable level.

EXAMPLE 7

Genomic DNA Transfections

In addition to electroporative transfection with an expression plasmid containing a gene of interest, cells may be transfected with whole genomic DNA containing a gene flanked by natural DNA sequences. Such DNA preparation will contain one or more copies of a gene in a very minor proportion (about 1 in 10,000) as compared to the total genomic DNA. However, if the transfection technique is very efficient, it is possible to detect a recipient cell which expresses protein encoded by the gene of interest.

The detection of cell surface receptor protein is especially convenient because, in this case, the expressed protein remains in association with the external cell surface of the expression host and can be detected by cell sorting (Radeke, M. J., et al. (1987), *Nature* 325, 593-597).

Figure 18:
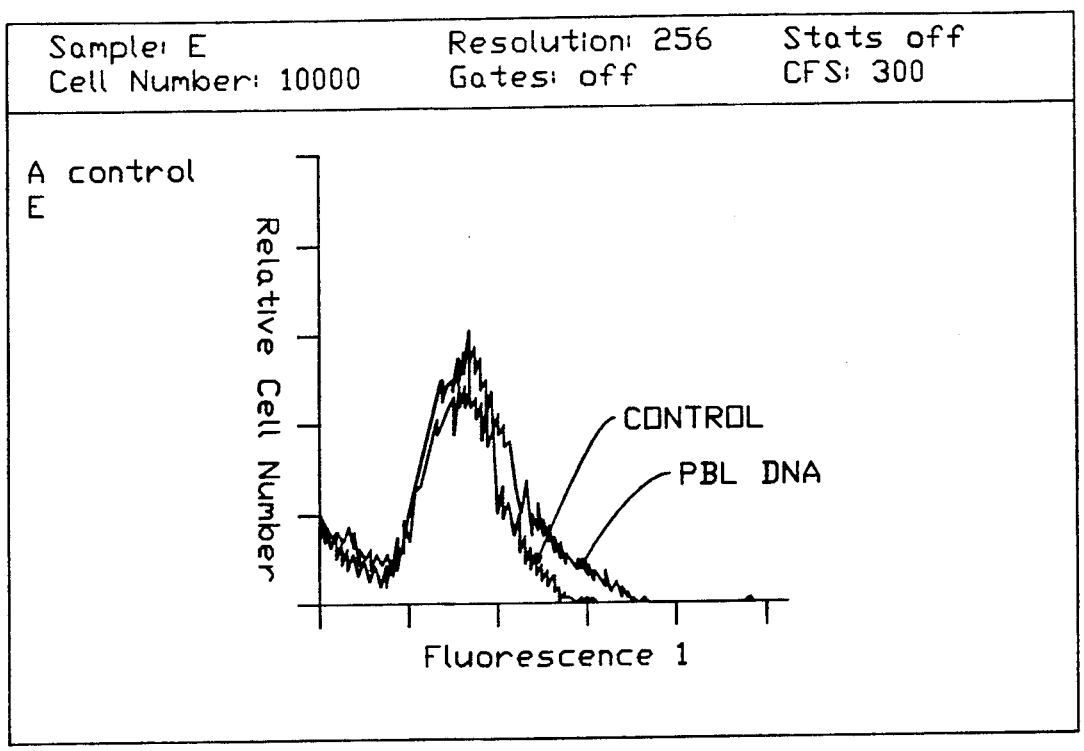
FIG. 18 is a cell-sort profile of CHO cells transfected with human genomic DNA.

FIG. 18 shows the result of such an experiment using the in situ electroporation of attached CHO cells and 20 μg human peripheral blood lymphocyte DNA, cotransfected with 5 mg of the selectable marker expression plasmid SV40-neo (Southern, et al., 1982). Selection was as in Example 2 and cells were harvested in PBS-1 mM EDTA. Cells were then stained in solution with biotinylated human IgE, followed by fluoroceine labelled avidin (Kikutani, H. et al. (1986), *Cell.* 47, 657-665). Cells expressing a functional IgE receptor, most likely the high affinity receptor described by Kanellopoulo, et al. (1980), *J. Biol. Chem.*, 255, 9060-9066; and Goetze, et al. (1981), *Biochemistry,* 20, 6341-6349, will stain positive in this technique.

The sorting profile shows a positive staining cell population on the first sort following selection. This may be compared with the results reported by Radeke, et al. (1987), *Nature,* 325, 593-597, where positive cells were seen only after multiple sorts. Since the transfection method used in that study was calcium phosphate, the present results indicate that the in situ electroporation method more efficiently transfected DNA into the CHO cells.

EXAMPLE 8

Attachment of Suspension Cells to the Growth Surface

The electroporation surface can be coated in order to promote adherence of suspension or attachment-dependent cells to the surface. Polylysine (Stulling, R. D., et al. (1973), *J. Exp. Med.* 137 932-942) and histones (Keay, L. (1975), *Tissue Cult Assoc.* 1, 177) have been used for this purpose.

In the histone method, a histone solution in PBS (taking special care to omit any trace calcium and magnesium) is placed on the surface and excess material rinsed off. Cells in growth medium are added and the cells allowed to settle to the bottom, where attachment takes place in minutes. Electroporation can be done immediately or after some period of cell growth. This attachment procedure allows the supernatant fluid (growth medium) to be easily changed to any other solution, if desired, for the electroporation procedure. In addition, when the electroporation involves a selectable marker contained on an expression plasmid the identification and isolation of transformed cells is greatly facilitated by their attachment to the growth surface (Keay (1975), *Tissue Cult Assn.* 1, 177).

Having described the preferred embodiments of the present invention, it will appear to those ordinarily skilled in the art that various modifications may be made to the disclosed embodiments and that such modifications are intended to be within the scope of the present invention.

The following publications are expressly incorporated herein by reference.

References

Breathnach, et al. (1981), *Ann. Rev. Biochem.* 50, 349
Capecchi, M. R. (1980), *Cell.* 22 479-488
Colbere-Garapin, F., et al. (1981), *J. Mol. Biol.* 50, 1-14
Gillis, S., et al. (1980), *J. Exp. Med.* 152, 1709-1719
Gorman, C. M., et al. (1985), *Cell,* 42. 519-526
Gorman, C. M., et al. (1982), *Mol. Cell. Biol.* 2, 1044-1051
Graham, F. L., et al. (1973), Virology, 52, 456-467
Keay, L. (1975), *Tissue Cult Assoc* 1, 177
Maroudas, N. G. (1977), *J. Theor. Biol.,* 49, 417-424
Maroudas, N. G. (1977), *J. Cell Physiol.,* 90, 511-519
McCutchan, J. H., et al. (1968), *J. Natl. Canc. Inc.,* 41, 351-357
Neumann, E., et al. (1982), *Eur. Mol. Biol. Org. J.,* 1, 841-845
Palmer, T. D., et al. (1987), *PNAS* 84, 1055-1059
Potter, H., et al. (1984), *Proc. Natl. Acad. Sci.,* 81. 7161-7165
Radeke, M. J., et al. (1987), *Nature* 325, 593-597
Scaffner, W. (1980), *Proc. Natl. Acad. Sci.,* 77, 2163-2167
Southern, P. J., et al. (1982), *J. Mol. Appl. Genet.* 1, 327-341
Stoker, et al. (1967), *Nature,* 215, 171-172
Stulling, R. D., et al. (1973) *J. Exp. Med.* 137, 932-942
Thilly, W. G. (1986) ed. "Mammalian Cell Technology", Butterworths, Boston
Urlaub, et al. (1980), *PNAS* 77, 4216
Voller, et al. (1976), *Bull World Health,* 53, 55-65
Weiss, R., et al. (1982) eds. "RNA Tumor Viruses", Cold Spring Harbor Laboratory, New York
Wong, T. K., et al. (1982), *Biochem. and Biophys. Research Commun.,* 107 584-587
Yalow, R. S., et al. (1960), *J. Clin. Invest.* 39, 1157
Yalow, R. S. (1978), *Science* 200 1236-1245

What is claimed is:

1. Electroporation apparatus comprising
   a flexible, substantially planar support member having a substantially non-conductive surface, and
   first electrode means comprising at least two electrically-connected substantially parallel electrodes disposed on said substantially non-conductive surface and second electrode means comprising at least two electrically-connected substantially parallel electrodes also disposed on the same surface as said first electrode means such that the electrodes of said first and second electrode means are alternately positioned on said surface.

2. The apparatus of claim 1 wherein said flexible support member is selected from the group consisting of mica, polyester and polystyrene.

3. The apparatus of claim 1 wherein said electrodes are disposed over substantially all of said non-conductive surface.

4. The apparatus of claim 3 wherein said apparatus substantially covers a planar surface of a container into which said apparatus is inserted.

5. The apparatus of claim 4 wherein said container is a petri dish and said apparatus is circular.

6. The apparatus of claim 1 wherein said electrodes of said first and said second electrode means have a width of about 10 $\mu$ and 2 mm.

7. The apparatus of claim 1 wherein said electrodes of said first and said second electrode means are positioned on said surface such that there is between 3 and 500 electrodes per centimeter on said surface.

8. The apparatus of claim 1 wherein said flat electrodes of said first and said second electrode means have a thickness of between about 1 to 100 thousands of an inch.

9. The apparatus of claim 1 in combination with fluid container means into which said apparatus is inserted.

10. The apparatus of claim 9 further comprising cells adhered to an inner surface of said fluid container means.

11. The apparatus of claim 1 wherein said electrodes are formed by deposition of a metallic material on said first or said second surface.

12. The apparatus of claim 1 wherein said electrodes are formed by selective etching of a metal surface attached to said first or said second surface.

13. The apparatus of claim 1 further including an adhesive backing for attaching said apparatus to the inner surface of said fluid container means, said adhesive backing being contained on a surface of said apparatus not containing said electrodes.

14. Electroporation process comprising
contacting cells adhered to a first surface with a fluid containing a substance, said first surface comprising an inner surface of an electroporation chamber, and
passing an electric impulse through said fluid to transfect said substance into at least one of said adhered cells, said electric impulse being produced by applying a first charge to first electrode means comprising at least two electrically-connected substantially parallel electrodes disposed on a second surface and a second opposite or neutral charge to second electrode means comprising at least two electrically-connected substantially parallel electrodes also disposed on said second surface such that electrodes of said first and said second electrode means are alternately positioned on said second surface, wherein said second surface is contained on a flexible, substantially planar, non-conductive support member capable of being inserted into said electroporation chamber so that said first and said second electrode means are in contact with said fluid.

15. Electroporation process comprising
contacting cells adhered to a first surface with a fluid containing a substance, and
passing an electric impulse through said fluid to transfect said substance into at least one of said adhered cells, said first surface comprising an inner surface of an electroporation chamber, said electric impulse being produced by applying a first charge to first electrode means comprising at least two electrically-connected substantially parallel electrodes disposed on said first surface and a second opposite or neutral charge to second electrode means comprising at least two electrically-connected substantially parallel electrodes also disposed on said first surface such that the electrodes of said first and said second electrode means are alternately positioned on said first surface.

16. Electroporation process comprising
contacting an electroporation chamber with a fluid containing a cell suspension and a biological substance, and
passing an electric pulse through said fluid to transfect said biological substance into at least one of said cells, said electric impulse being produced by applying a first charge to first electrode means comprising at least two electrically-connected substantially parallel electrodes disposed on a first surface and a second opposite or neutral charge to second electrode means comprising at least two electrically-connected substantially parallel electrodes also disposed on said first surface such that the electrodes of said first and said second electrode means are alternately positioned on said first surface, said first surface being contained on a substantially planar, non-conductive support member.

17. The process of claim 14, 15 or 16 wherein said attached cell is a mammalian cell.

18. Electroporation apparatus comprising
an electroporation chamber comprising a first surface having cells adhered thereto,
a fluid in contact with said adhered cells, and
first electrode means comprising at least two electrically-connected substantially parallel electrodes disposed on said first surface and second electrode means comprising at least two electrically-connected substantially parallel electrodes also disposed on said first surface such that the electrodes of said first and said second electrode means are alternately positioned on said surface and are in contact with said fluid.

19. Electroporation apparatus comprising
an electroporation chamber containing a first substantially planar inner surface having cells adhered thereto,
a fluid in contact with said adhered cells, and
first electrode means comprising at least two electrically-connected substantially parallel electrodes disposed on a second surface and second electrode means comprising at least two electrically-connected substantially parallel electrodes also disposed on said second surface such that the electrodes of said first and said second electrode means are alternately positioned on said second surface, wherein said second surface is contained on a flexible, substantially planar non-conductive support member capable of being inserted into said electroporation chamber so that said first and said second electrode means are in contact with said fluid in said electroporation chamber.

20. Electroporation apparatus comprising
an electroporation chamber,
a substantially planar non-conductive support member contained in said electroporation chamber having a first surface with cells adhered thereto,
a fluid in contact with adhered cells, and
first electrode means comprising at least two electrically-connected substantially parallel electrodes disposed on said first surface and second electrode means comprising at least two electrically-connected substantially parallel electrodes also disposed on said first surface such that the electrodes of said first and said second electrode means are alternately positioned on said first surface and are in contact with said fluid.

21. The apparatus of claims 18, 19 or 20 wherein said electrodes of said first and said second electrode means are positioned so that there is between 3 and 500 electrodes per centimeter on said surface.

22. Electroporation process comprising
contacting an electroporation chamber with a fluid containing a cell suspension and a biological substance, and
passing an electric impulse through said fluid to transfect said biological substance into at least one of said cells, said electric impulse being produced by applying a first charge to first electrode means comprising at least two electrically-connected substantially parallel electrodes disposed on a surface of a flexible, substantially planar, non-conductive support member and a second opposite or neutral charge to second electrode means comprising at least two electrically-connected substantially parallel electrodes also disposed on said surface such that electrodes of said first and said second electrode means are alternately positioned on said surface, said electrodes of said first and said second electrode means being in contact with said fluid when said non-conductive support member is inserted into said electroporation chamber.

23. Electroporation process comprising
contacting cells adhered to a first surface with a fluid containing a substance, and
passing an electric impulse through said fluid to transfect said substance into at least one of said adhered cells, said electric impulse being produced by applying a first charge to first electrode means comprising at least two electrically-connected substantially parallel electrodes disposed on said first surface and a second opposite or neutral charge to second electrode means comprising at least two electrically-connected substantially parallel electrodes also disposed on said first surface such that the electrodes of said first and said second electrode means are alternately positioned on said first surface, said first surface being contained on a substantially planar, non-conductive support member.

* * * * *

UNITED STATES PATENT AND TRADEMARK OFFICE
CERTIFICATE OF CORRECTION

PATENT NO. : 5,128,257

DATED : July 7, 1992

INVENTOR(S) : Bradford W. Baer

It is certified that error appears in the above-indentified patent and that said Letters Patent is hereby corrected as shown below:

Column 7, line 61, change "A" to read --As--.

Column 10, line 42, delete "t".

Column 10, line 43, change "is" to read --this--.

Column 13, about line 28, change "(2 X 10 cells)" to read --(2 X $10^6$ cells)--.

UNITED STATES PATENT AND TRADEMARK OFFICE
CERTIFICATE OF CORRECTION

PATENT NO. : 5,128,257
DATED : July 7, 1992
INVENTOR(S) : Bradford W. Baer

It is certified that error appears in the above-indentified patent and that said Letters Patent is hereby corrected as shown below:

Column 13, about line 50, change "106 cells/ml" to read --$10^6$ cells/ml--.

Column 13, about line 60, delete "$\beta$".

Column 13, about line 60, change "TFG" to read --TGF$\beta$--.

Signed and Sealed this

Sixteenth Day of August, 1994

Attest:

BRUCE LEHMAN

Attesting Officer    Commissioner of Patents and Trademarks